(12) United States Patent
Glisson

(10) Patent No.: US 7,298,872 B2
(45) Date of Patent: Nov. 20, 2007

(54) ELECTRONIC IDENTIFICATION SYSTEM FOR FORM LOCATION, ORGANIZATION, AND ENDORSMENT

(76) Inventor: Shawn Glisson, 805 Oxmoor Wood Pkwy., Louisville, KY (US) 40222

( * ) Notice: Subject to any disclaimer, the term of this patent is extended or adjusted under 35 U.S.C. 154(b) by 248 days.

(21) Appl. No.: 10/920,078

(22) Filed: Aug. 17, 2004

(65) Prior Publication Data

US 2006/0064392 A1    Mar. 23, 2006

(51) Int. Cl.
*G06K 9/00*    (2006.01)
*G05B 19/00*    (2006.01)

(52) U.S. Cl. .................... 382/115; 340/5.81; 902/3; 902/5

(58) Field of Classification Search ............ None
See application file for complete search history.

(56) References Cited

U.S. PATENT DOCUMENTS 5,857,028 A * 1/1999 Frieling ................. 382/116

6,976,162 B1 * 12/2005 Ellison et al. .......... 713/156
2002/0035485 A1 * 3/2002 Mita et al. ............. 705/2
2004/0003072 A1 * 1/2004 Mathew et al. ........ 709/223
2004/0006553 A1 * 1/2004 de Vries et al. ........ 707/1

* cited by examiner

*Primary Examiner*—Bhavesh M Mehta
*Assistant Examiner*—Charles Kim
(74) *Attorney, Agent, or Firm*—Dinsmore & Shohl LLP; Denise M. Everett

(57) ABSTRACT

Disclosed is a secure system of authentication including a means for retrieving information about an authenticated individual (i.e., citizens, customers, employees, patients, and subjects). More specifically, the system allows a person to execute forms (i.e., agreements, authorizations, contracts, records, and transactions) at any location across the world by submitting to a positive identification test. In turn, authorized personnel can receive all pertinent information associated with the authenticated individual. Importantly, the autonomy and the privacy of the individual with respect to his or her information are always maintained.

16 Claims, 16 Drawing Sheets

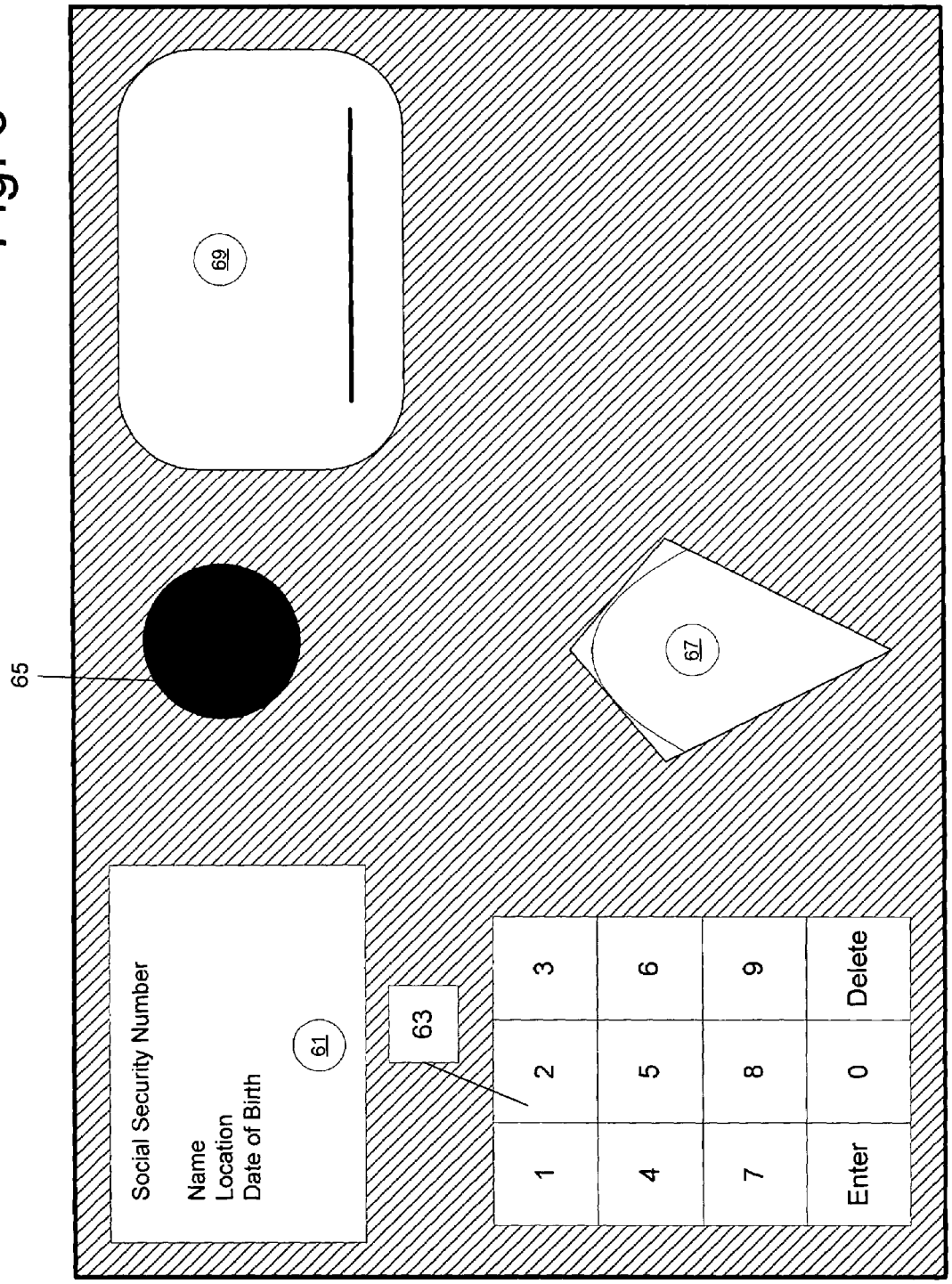

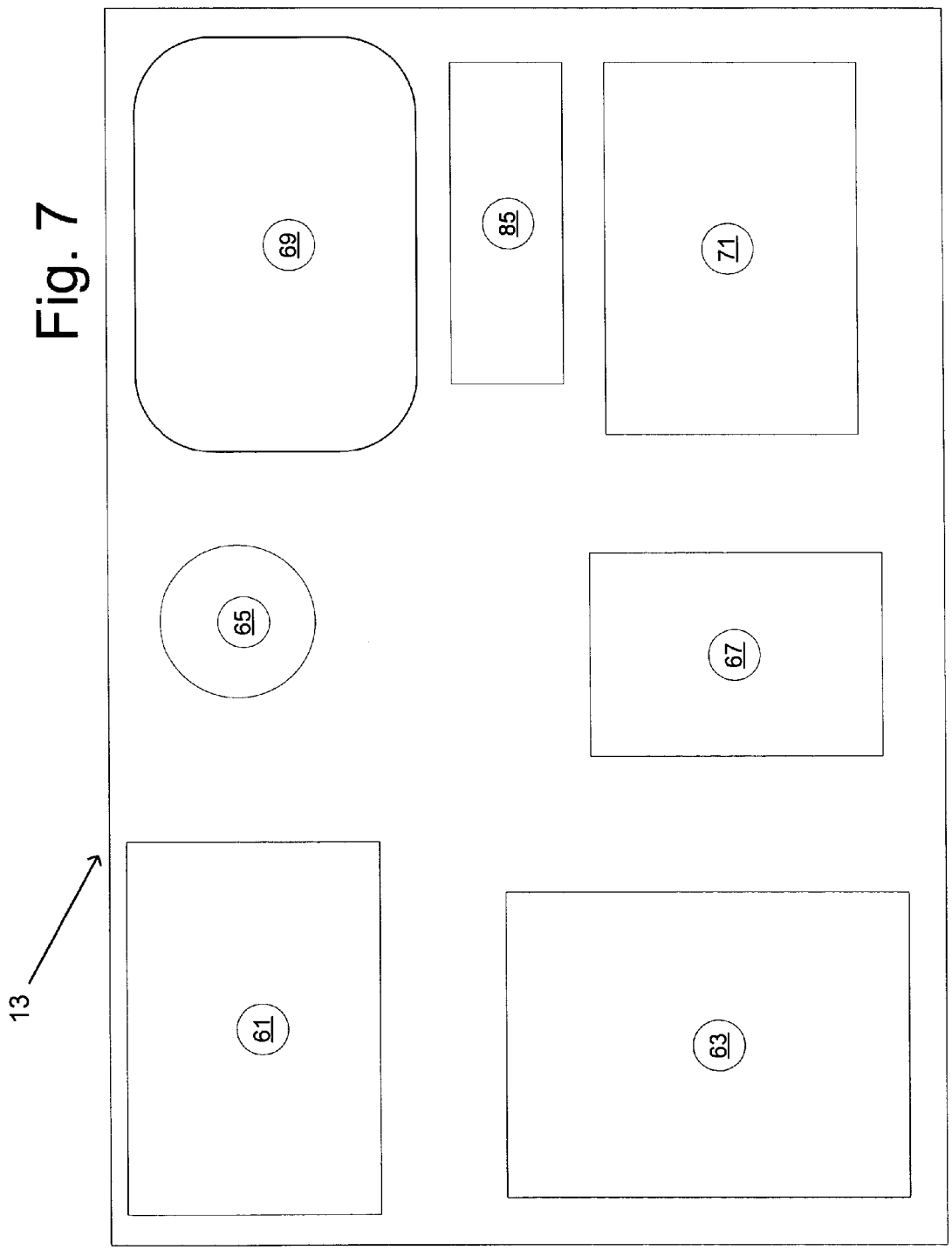

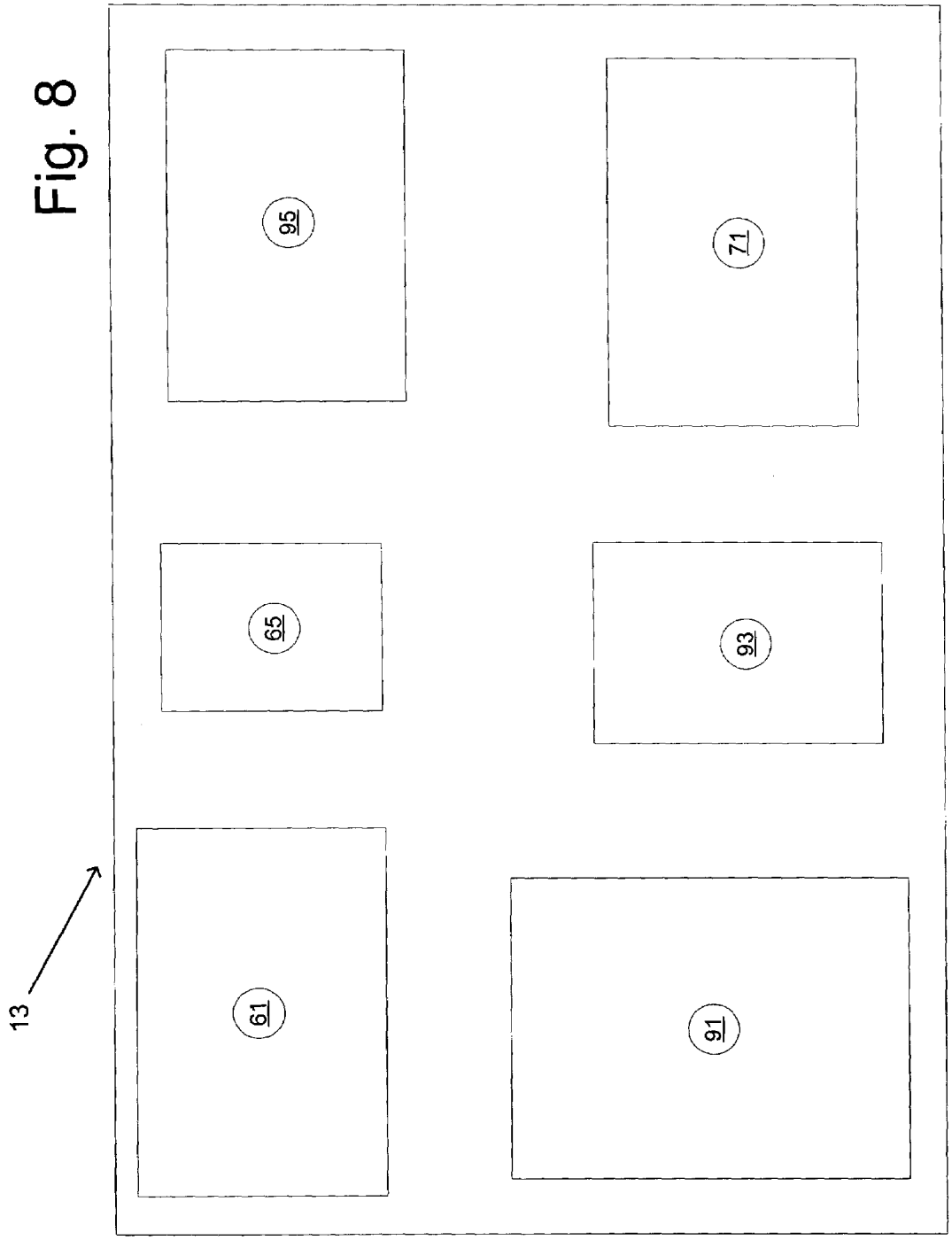

ELECTRONIC IDENTIFICATION SYSTEM FOR FORM LOCATION, ORGANIZATION, AND ENDORSMENT

TECHNICAL FIELD OF THE INVENTION

This invention relates to a system and method for positively identifying individuals (i.e., citizens, customers, employees, patients, and subjects) at particular points of interest in the areas of health care (e.g., hospitals or doctor's offices), security (e.g., banks, airports, etc.), and any other situations where an individual's identity must be confirmed. This invention further relates to a database that contains individual biometric data along with commonly accessed identifying information about the individual. The additional identifying information is contained in another category of databases that manage information about individuals including, but not limited to, health care information, security issue information, and any other private information which an individual wants to protect.

BACKGROUND OF THE PRESENT INVENTION

In today's society, it is becoming increasingly important for entities to accurately confirm the identity of individuals. This is made clear especially in three areas of challenge to current society: 1) the passage and maintenance of health care records; 2) the problem of identity theft to criminals and loss of control of identity in reference to other individuals or entities in society; and 3) security issues of national protection as required by certain functions (e.g., such as opening a bank account must now be monitored).

In general, society currently relies on the confirmation of individuals through witnesses, identity cards, identity codes, and biometric identifiers. For example, a witness, (e.g., anyone from a casual acquaintance to a notary public) can confirm a person's identity. Also, identity cards and personal identification codes are utilized to authenticate an individual's identity. This system, however, is expensive and corruptible. Recognizing these deficiencies, attempts have been made to improve the situation.

One example of a present identification system is a computer system that remotely records the arrival and departure times of field-based employees at various work sites through a telephone network. Specifically, the system detects an employee's automatic number identification data and further collects personal identification codes from the caller. The automatic number identification and personal identification code are used to identify the calling telephone. Once identified, the system can record the arrival and departure times of the employee.

These systems have several disadvantages. First, automatic number identification (i.e. "Caller ID") only indicates the telephone number of the particular telephone used to make the call. Automatic number identification information therefore does not affirmatively confirm the identity of an individual—only the location from which the individual is placing a telephone call. Similarly, personal identification codes are manually entered into a keypad by any individual and are therefore not reliable for confirming the identity of an individual. More specifically, mere receipt of a manually entered personal identification code does not assure that the person entering the personal identification code is the person assigned to the personal identification code.

Because these above systems are expensive, time consuming, or subject to misuse and abuse, biometric devices were created for use in identification and authorization. Generally, measurable and recordable body features (e.g., fingerprints, eye patterns, facial contours, or voice characteristics, etc.) are registered as biometric keys and, at the time of authentication, compared with the respective body features of a person to be authenticated.

A personal computer ("PC") can be equipped with a device (e.g., a video camera) that makes it possible for the PC to record biometric information (e.g., facial features) and to reuse the information at a later time for authenticating an individual. The PC could grant access to a user only if it confirms the identity of the user by recognizing his or her facial features.

In any event, the above identification systems are currently used only on an ad hoc basis and are not connected to any national database. Furthermore, if a national database were implemented according to today's technology, the holder of the end data would not only have the individual's acquired data, but also the individual's unique identification information. Such systems do not protect the individual from fraud and abuse. Such systems cannot be currently regulated by US law to protect the identity of the individual from being passed to other entities. Over time the independence of the individual would be lost. In addition, they are also subject to fraud and abuse if implemented without a secured input device.

There currently exists a need for a national or international system that would allow authentication of an individual at any given time and location while at the same time protecting the individual from loss of identity. On 27 Apr. 2004, President Bush called for the majority of Americans to have interoperable electronic health records within ten years. David J. Brailer, M.D., Ph.D., National Coordinator for Health Information Technology, released his report, "The Decade of Health Information Technology: Delivering Consumer-centric and Information-rich Health Care," on 21 Jul. 2004. In the report he calls for four goals in the strategic framework: 1) Informed Clinical Practice; 2) Interconnected Clinicians; 3) Personalized Care; and 4) Improved Population Health.

"The Uniting and Strengthening of America by Providing Appropriate Tools Required to Interrupt and Obstruct Terrorism" (USA Patriot Act) Act of 2001 (H.R. 3162-24 Oct. 2001) requires, among other things, the identification and verification by all financial institutions of accountholders and prospective accountholders (See, §326). Not only must an accountholder be identified and verified, records related to the accountholder, at a minimum name, address and other identifying information, must be maintained. In other words, a secure database is required.

Databases have been utilized for a number of years to store, sort and distribute information. Specifically, in the medical field, databases have been utilized to diagnose and treat patient diseases. David Bennahum illustrates the long known need for medical interconnectivity in an article entitled "Docs for Docs" in Wired Magazine in June 1995. He notes that doctors have been attempting to create a "virtual patient record" for years. Essentially, with the emergence of more efficient wireless networks, it was possible to link doctors, hospitals, insurance companies, and drug labs. As a result, doctors were able to record instructions, maintain medical information and receive general medical information from insurance companies and drug labs over a wireless network connecting several databases. Unfortunately, the system of interconnectivity has never occurred because the current system of authentication and security of the information electronically can not be secured in a timely, inexpensive manner that will not allow the possibility of identity loss.

There exists a need for a system that positively authenticates an individual and that is connected to a database for immediate retrieval of an individual's medical information. More specifically, patients visiting such places as doctor's offices, dentist's offices and hospitals often need to complete forms they have completed in the past. A system that positively identifies an individual and that retrieves all pertinent information about the individual (e.g., name, insurance carrier, etc.) is greatly desired provided identity loss cannot occur.

There exists a need for a secured system that allows an employee, client, patient, subject or citizen to interface with an organization, business, individual, or government agency when a positive identification for a form to be completed is required. Such form collections, authorizations, verifications and organization are increasingly costly and difficult to manage in a secure fashion. As more and more human abstract thought and information leaves the confines of the visible universe and enters the electronic "fifth dimension" in an ever growing world that occupies neither space nor time, where information about every individual can, as an electron around an atom, be every where and no where at the same time, it is important in the preservation of liberty that each individual's fifth dimension of abstract thought and information be protected and preserved as his or her own.

SUMMARY OF THE INVENTION

The present invention relates generally to a system of authentication and a means for retrieving information about the authenticated individual. More specifically, it allows a person to execute forms (e.g., consent forms) at any location across the world by submitting to a positive identification test. In turn, doctors and medical researchers can, for example, receive all pertinent information associated with the authenticated individual (e.g., medical history, allergies, consent forms, etc.).

The present invention relates to an inexpensive and secure system that can positively authenticate an individual and retrieve pertinent information regarding that individual while leaving his or her fifth dimension of abstract knowledge and information secured. The present invention further allows an entity to interact with the general population to retrieve, process, and organize secured completed forms in a way that allow centralization of information while protecting the autonomy of the individual.

An object of the present invention is to provide a system to allow an employee, client, patient, subject, or citizen to interface with an organization, business, individual, or government agency when a positive identification for a form to be completed is required. Another object of the present invention is to provide assured confirmation of an individual via a secure, tamper-proof system.

Yet another object of the present invention is to provide a system that can transmit its location when accessed to confirm the identity of the active user.

Yet another object of the present invention is to allow any entity (e.g., organization, business, individual, or government agency) that requires an individual to complete a form to ensure that the forms are properly signed and the identity of the signatory is verified.

Yet another object of the present invention is to allow any equipped entity (having the permission and verification of an individual) to access the individual's pertinent information, including all forms completed by the individual.

Another object of the present invention is to allow an individual to alter his or her pertinent information from a properly equipped personal computer.

Yet another object of the present invention is to allow an individual to fill out pertinent forms (i.e. agreements, authorizations, contracts, records, and transactions) at a convenient time and place.

Yet another object of the present invention is to allow communication of an individual's secured information from one Electronic Identification System's Biometrically Endorsed Repository Grid ("EISBERG") to another, if he or she so chooses. If this decision is not made by the individual, then no communication may be made from an EISBERG with any other entity.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 5 depicts a top view of the preferred embodiment of the Electronic Identification System Machine ("EIS Machine") for interfacing between an individual and the system of the present invention, showing means for collecting information (including biometric information) from an individual for verification purposes.

FIG. 7 depicts an example of internal components of the interface of the preferred embodiment of the present invention for securely retrieving and utilizing an individual's biometric information for authenticating an individual.

FIG. 8 depicts an example of internal components of the interface of an alternate embodiment of the present invention for securely retrieving and utilizing an individual's biometric information for authenticating an individual.

DETAILED DESCRIPTION OF THE PREFERRED EMBODIMENTS

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present invention. The following presents a detailed description of a preferred embodiment (as well as some alternative embodiments) of the present invention.

Figure 1:
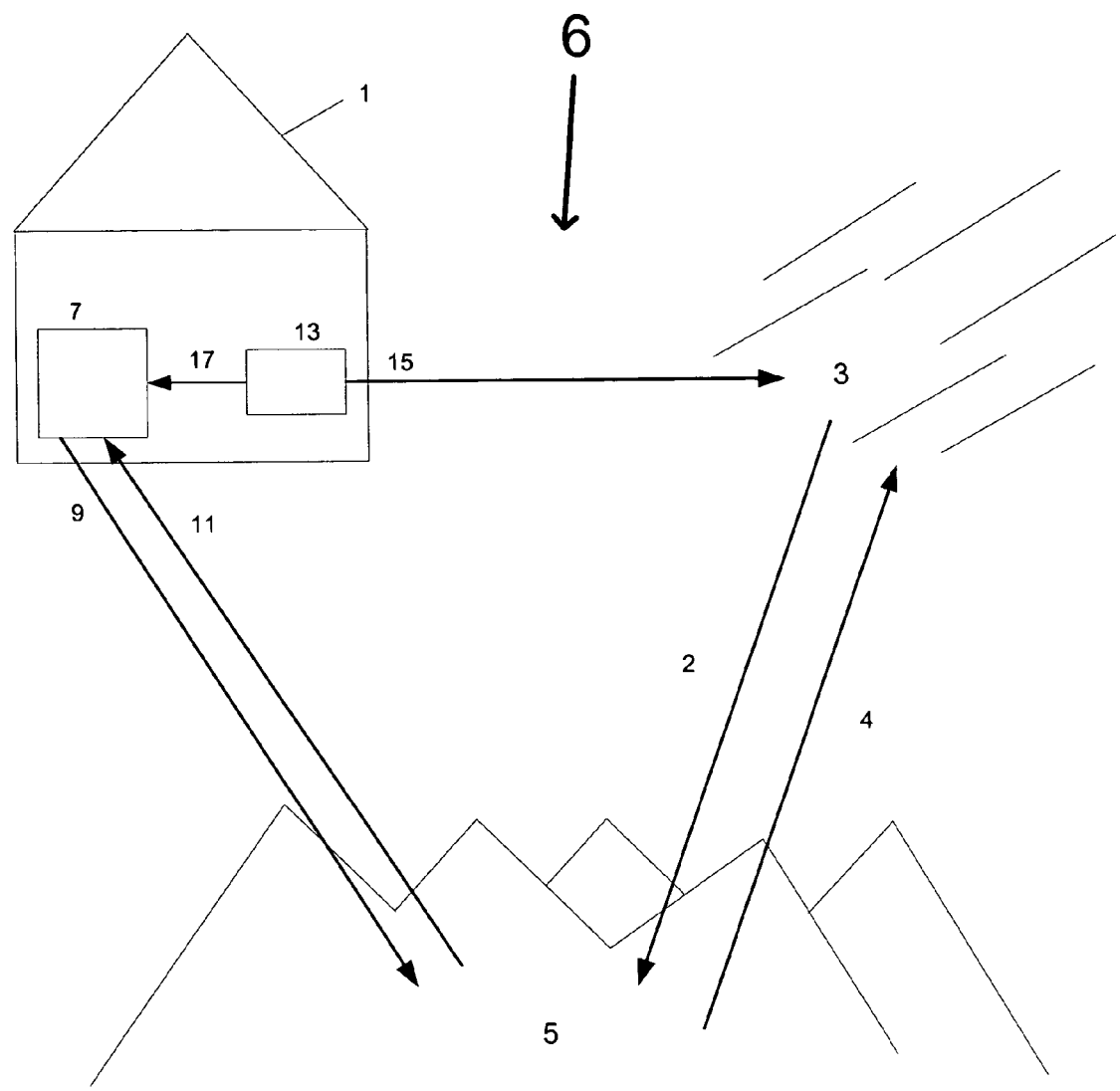
FIG. 1 depicts an example of the Electronic Identification System for Form Location, Organization and Endorsement ("EISFLOE") showing the flow of authentication and biometric parameter information between the components of the system.
Figure 2:
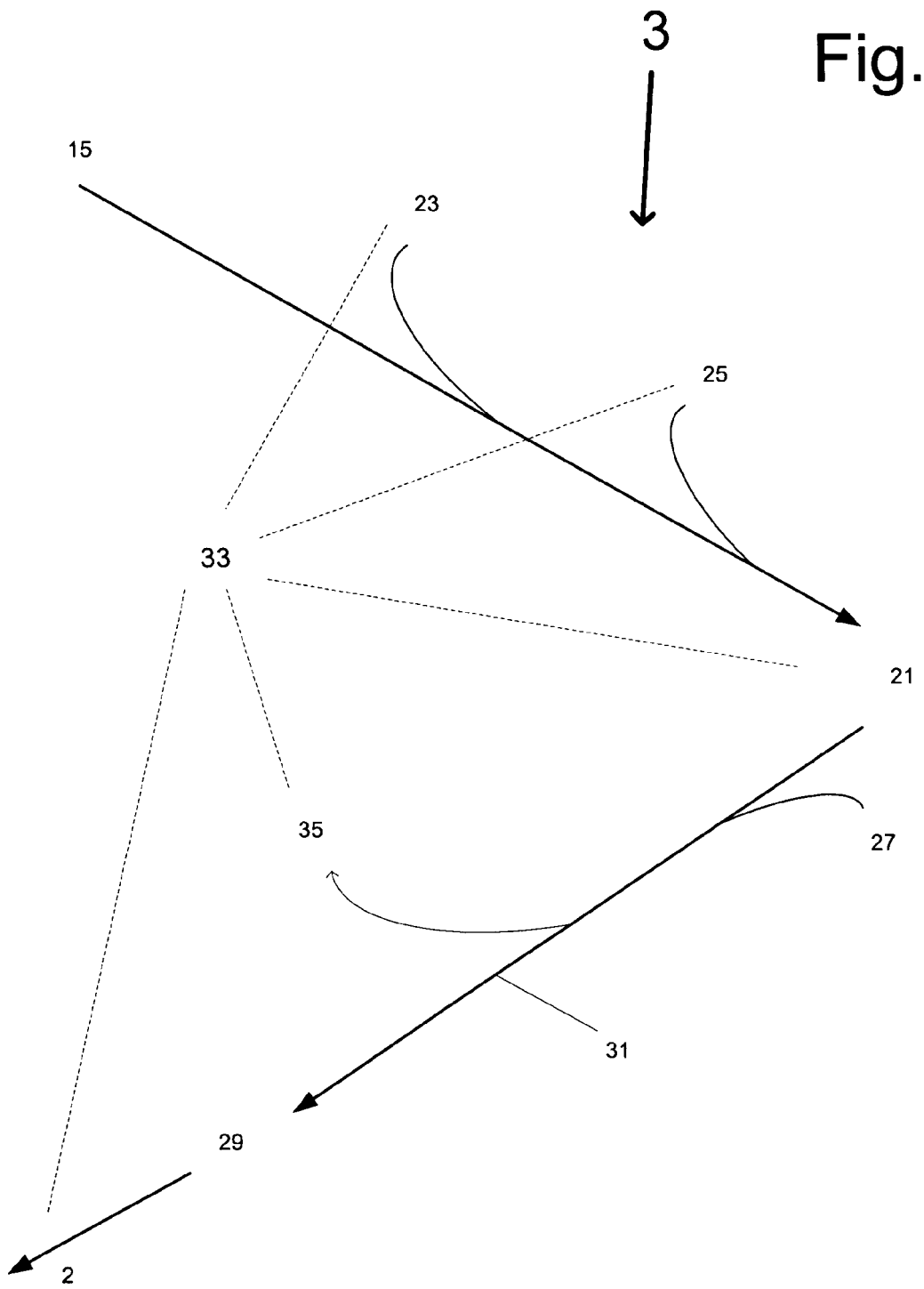
FIG. 2 depicts an example of the Electronic Identification System's Comprehensive Authentication Process ("EIS-CAP") that links an individual's biometric parameters with another piece of identification information in order to authenticate an individual in accordance with the invention.

Referring first to FIGS. 1 and 2, an overview of the preferred embodiment of the present invention is depicted at the point of access by an individual. More specifically, the Electronic Identification System for Form Location, Organization and Endorsement ("EISFLOE") 6 is shown, generally comprising three components: the point-of-access by a user of the system in EIS House 1, Electronic Identification System's Comprehensive Authentication Process ("EISCAP") 3, and Electronic Identification System's Biometrically Endorsed Repository Grid ("EISBERG") 5, each of which will be described in more detail below.

EIS House 1 serves as the site where the user elects to authenticate a form. The meaning of "form," includes but is not limited to, agreements, authorizations, contracts, records, and transactions relating to all aspects of the Automated Numerical Identifier Network ("ANI Network") (as defined below). A form may embody a physical document or alternatively an electronic document (e.g., a fillable internet webpage). Internet Access Device ("IAD") 7 (e.g., a computer terminal) and EIS Machine 13 interact within EIS House 1. Importantly, EIS Machine 13 receives no electronic data input. Through communication line 17, EIS Machine 13 interfaces with IAD 7 when called upon by EISBERG 5, requesting that the individual enter his or her electronic identity into EIS Machine 13. Once the individual activates EIS Machine 13, the electronic message is attached to a web page in IAD 7 and sent through communication line 9 to EISBERG 5. Simultaneously EIS Machine 13 sends the electronic identity out of EIS House 1 to EISCAP 3 through communication line 15, as noted below, which is discussed in greater detail below.

Generally, a user of the system of the present invention wishes to authorize a specific form (e.g., consent form, tissue donation authorization form, do not resuscitate form, etc.) and accesses the system of the present invention at EIS House 1, via IAD 7. The information regarding the specific form can be collected in any manner as described in greater detail below. Initially, IAD 7 transmits information regarding the requested form over communication line 9 to EISBERG 5. In response, EISBERG 5 retrieves the requested form from an internal storage area (e.g., database) and transmits the corresponding form information over communication line 11 to IAD 7. The user utilizes an interface device, such as a terminal, at EIS House 1 to supply the information required by the form and utilizes EIS Machine 13 to initiate authentication of the form. Generally, EIS Machine 13 transfers an electronic code along with the form from IAD 7 to EISBERG 5 while simultaneously transferring a coded signal containing a user's biometric and identification information over communication line 15 to EISCAP 3.

As described above, in the preferred embodiment of the present invention an individual requests a form (e.g., a web page form) via IAD 7. IAD 7 can comprise any computer means connected to EIS Machine 13 that is equipped with the proper identification peripherals as described in greater detail below.

Although all communication lines are depicted as physically connected communication means, it is contemplated that all communication within the system of the present invention can be completed by any method of information transfer, including but not limited to telephone trunk lines, T1 data lines, and wireless communication means.

Generally, as shown in FIG. 1, EIS House 1 includes Internet Access Device ("IAD") 7 and EIS Machine 13 and may be located anywhere in the world. EIS Machine 13 provides a secured means for an individual to interface with an organization, business, individual, or government agency when a positive identification for a form to be completed is required. Because EIS Machine 13 is tamper-proof and will transmit its location when accessed, the active participation of the person being identified (i.e., the user) can be assured.

EIS Machine 13 is registered with EISFLOE system 6 and is assigned a unique identification code to confirm access when transmitting information to EISCAP 3 or EISBERG 5. To access EISFLOE 6, an individual who wishes to consider authorizing a form accesses IAD 7 by utilizing an interface (i.e., a terminal) in EIS House 1. The user can enter information to indicate the desired form through any known means of collecting information, including, but not limited to, digital scan and keyboard means. EIS Machine 13 is capable of interfacing with IAD 7 in transmitting the response to a form that requires authentication over communication line 17 via IAD 7 to EISBERG 5 over communication line 9.

EIS machine 13 also collects a user's identification information, which can be in the form of a number or other data. In the preferred embodiment, a user's identification information is the user's Social Security Number, but in alternative embodiments, a user's identification information may comprise a unique number assigned to the user or any other information that serves to uniquely identify the user (e.g., passport number, etc.). In addition, EIS machine 13 may collect a user's biometric information (e.g., digital picture, fingerprint, signature, DNA, etc.). Preferably, EIS Machine 13 is capable of transmitting a user's biometric information to EISCAP 3 over communication line 15. In the preferred embodiment, EIS machine 13 is incapable of receiving any electronically transmitted information.

While transferring the user's identification and biometric information to EISCAP 3, EIS Machine 13 authorizes IAD 7 to transmit the completed form to EISBERG 5 via communication line 9. EISBERG 5 then awaits authentication from EISCAP 3 via communication line 4. Once EISCAP 3 verifies the identity of the user, it communicates back to EISBERG 5 via communication line 2. The signal that the form has been successfully completed is then sent via communication line 11.

Figure 3:
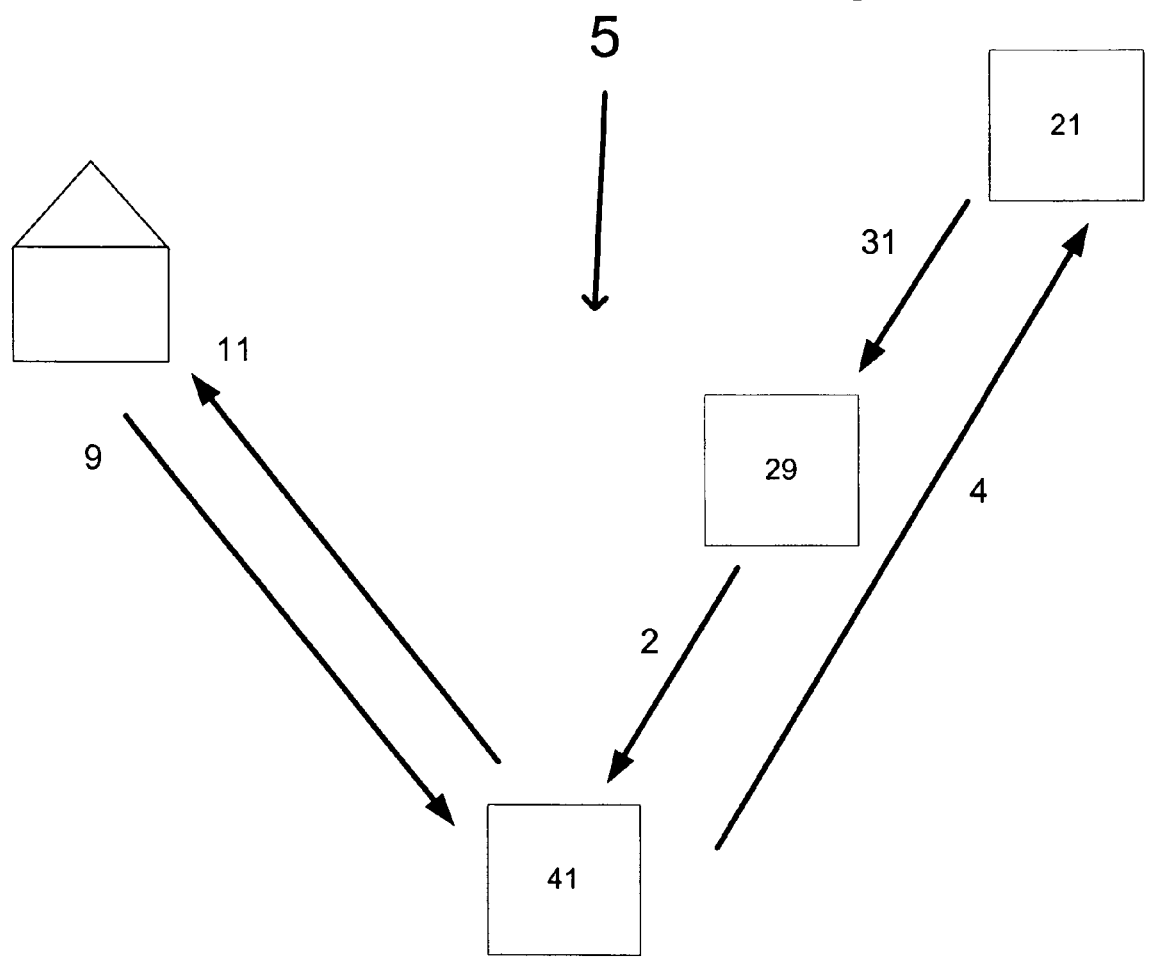
FIG. 3 depicts an example of the Electronic Identification System's Biometrically Endorsed Repository Grid ("EISBERG") that allows an individual to complete specific forms (e.g., consent forms) by connecting to a secure database according to the preferred embodiment of the present invention.

Referring now to FIG. 2, the system and method of authenticating the user via EISCAP 3 is shown. This is where the individual is judged to be authentic. Generally, EISCAP 3 is the system of connections between databases containing user identification numbers, biometric information, and other identifiers (both biometric and non-biometric). More specifically, EISCAP Server 21 receives the identification and biometric information from EIS Machine 13 via communication line 15. Additional information, such as the location of EIS Machine 13 (sent by Global Positioning System ("GPS") 23) and the time of access (sent by atomic clock 25) are recorded in EISCAP Server 21 with the biometric and identification information sent from EIS Machine 13. This grouping of information serves to uniquely identify the transaction and is assigned tracking number 27. The grouping of information ("EISCUBE" 29) is sent to EISBERG Server 41 via communication line 31, as depicted in FIG. 3. In such a way, EISCAP 3 verifies the identity of the user of EIS Machine 13 in an accurate manner.

In the preferred embodiment of the present invention, EISCAP 3 further comprises security monitoring system 33 that tracks the input of information over communication line 15, GPS 23, and atomic clock 25. EISCAP 3 records the transfer of information between EIS Machine 13 and EISCAP 3 in EISCAP database 35. Security monitoring system 33 further recognizes any irregular information and isolates any potential errors for review. By recording potential errors in EISCAP database 35, security monitoring system 33 ensures that EISCAP 3 can provide accurate authentication information in a secure manner.

Referring next to FIG. 3, EISBERG 5 performs the function of managing the forms that require authentication. For example, EISBERG 5 contains a plurality of forms (e.g., consent forms for treatment, do not resuscitate forms, etc.) that require an individual's consent for execution. Different EISBERGs can be connected to EISFLOE system 6 based on desired function. For example, different EISBERGs can include: (1) Tissue Donation/Consent for Cancer Research (or other medical illness research); (2) Medical Outcome Data Consent Form; (3) Medical Procedure Consent Form; (4) HIPAA compliance in medical offices, clinics, hospitals, etc.; (5) Insurance fraud prevention; (6) Sign-in system for employees/customers; (7) Verification for services rendered at a given time and place; and (8) Organ Donation for state non-profit organ donation organizations for organ procurement.

As shown, in the preferred embodiment of the present invention, EISBERG 5 comprises EISBERG Server 41 for sending and receiving information via communication lines 2, 4, 9, and 11. Generally, as described in greater detail with respect to FIG. 1, EISBERG 5 receives information from IAD 7 corresponding to the form requested by the user and transmits the requested form to IAD 7 via communication line 11. Once the user completes the form using the inputs at EIS Machine 13, IAD 7 transmits the completed form to EISBERG Server 41 to await authentication. Authentication occurs when EISBERG Server 41 communicates with EISCAP Server 21 via communication line 4. Then as also described in greater detail with respect to FIG. 2, EISBERG 5 receives information from EISCAP 3 (i.e., EISCUBE 29) verifying the identity of the user.

More specifically, EISBERG Server 41 receives and stores completed form information provided by IAD 7 over communication line 9. EISBERG Server 41 further receives and stores EISCUBE 29 from EISCAP 3 over communication line 2.

EISBERG Server 41 reviews EISCUBE 29 to ensure that the user has agreed to the content in the form transmitted to EISBERG 5 from IAD 7. Once EISCUBE 29 is verified, EISBERG Server 41 matches EISCUBE 29 with the completed form sent to EISBERG 5 by IAD 7 and attaches EISCUBE 29 to the completed form to create a verified form. This verified form may then be retrieved at IAD 7 for internal use in EIS House 1 via communication line 11.

It should be noted that signature information and photographic information can be collected-at EIS Machine 13 and utilized in the verification process in EISCAP 5. Such signature and photographic information could be included in EISCUBE 29 and attached as part of the verified form in EISBERG 5. All information received by EISBERG 5 (typically confidential or individual-sensitive information) remains within EISBERG Server 41 and can be used only in accordance with the agreement made with the individual. Such information is not transmitted to EISCAP 3.

There is also a security program that runs at the EISCAP 3 for monitoring the system of EIS Machines and EISBERGs.

Figure 4:
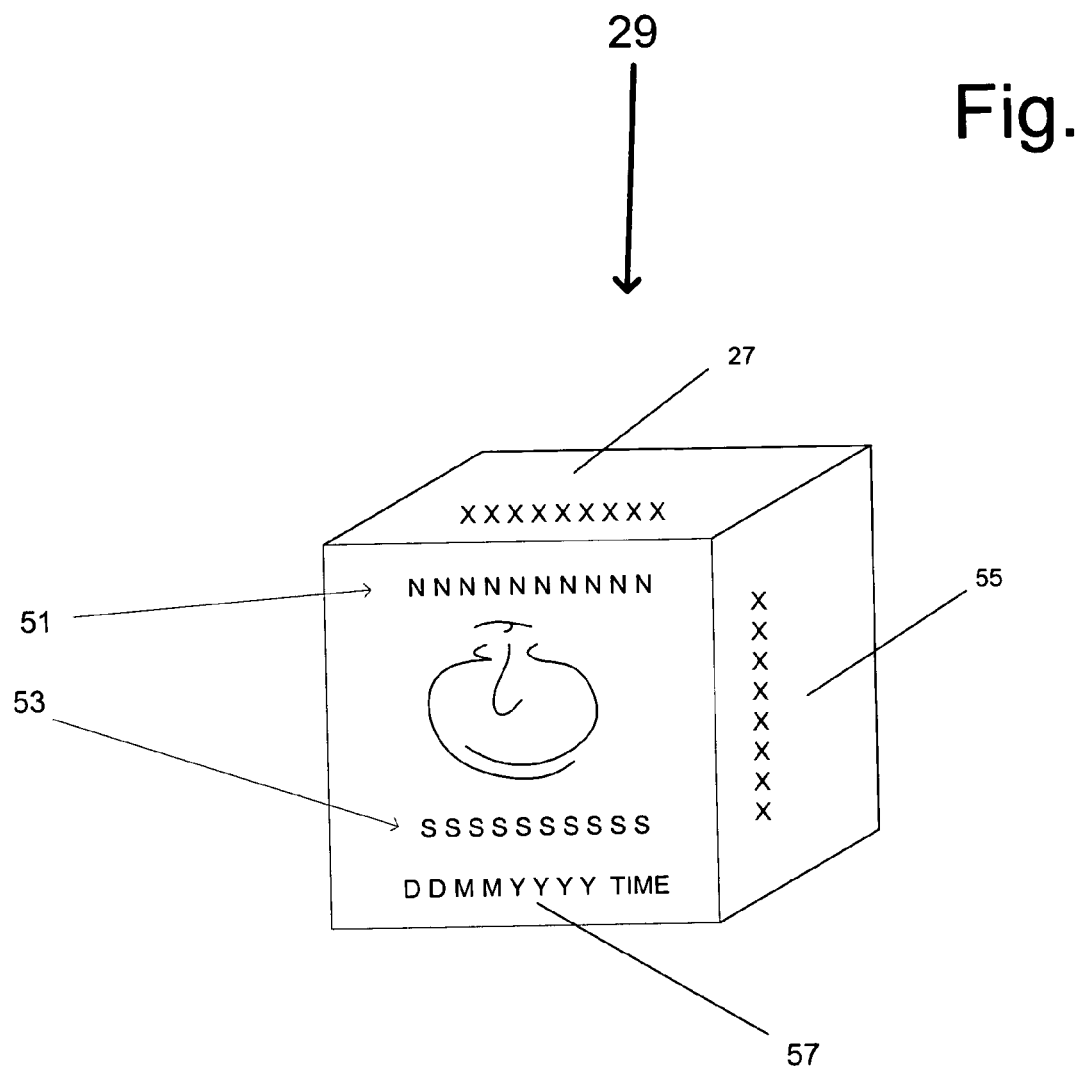
FIG. 4 depicts an example of an Electronic Identification System's Confirmed Unique Biometric Encounter ("EISCUBE") for documenting the authentication of an individual according to the preferred embodiment of the present invention.

Referring next to FIG. 4, shown is EISCUBE 29 utilized for authentication of the user at EIS Machine 13. Specifically, EISCUBE 29 contains information such that the individual user can be positively authenticated. EISCUBE 29 is attached to a verified form to indicate that the form has been authenticated. Although EISCUBE 29 can comprise any number of personal identifiers, in the preferred embodiment depicted in FIG. 4, EISCUBE 29 comprises user name 51, user signature 53, tracking number code 27, grid coordinates 55, and date and time of transaction 57. EISBERG 5 attaches EISCUBE 29 to the proper form as a symbol to the EISFLOW system that the user has been authenticated and verified the information contained in the form.

Referring now to FIG. 5, one embodiment of EIS Machine 13 is depicted. Specifically, FIG. 5 shows an example of the terminal associated with EIS Machine 13, designed to receive identification and biometric information from the user. Shown is Liquid Crystal Display ("LCD") 61 for display of requested information, EIS Keys 63 for entry of identification information, digital camera 65 for recording of biometric information such as facial features, EIS Crystal 67 for recording the user's fingerprint information, and EIS Rink 69 for entry of a user's signature. The inputted information is sent to EISCAP 3 as detailed above with respect to FIG. 1. The cover of EIS Machine 13 is preferably fastened in such a way that it cannot be opened without deactivating the system.

Figure 6A:
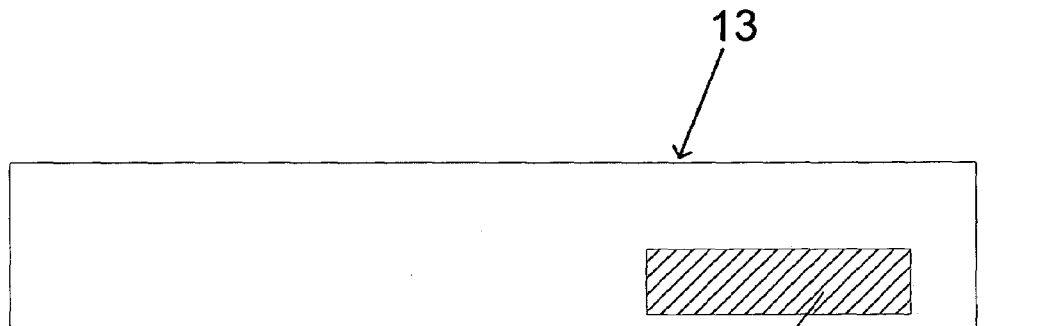
FIG. 6A depicts a front view of the interface of the preferred embodiment of the present invention, having a means for reading an identification card to authenticate the identity of an individual.

Referring next to FIG. 6A, a front view of EIS Machine 13 is depicted. Specifically, in the preferred embodiment of the present invention, EIS Machine 13 is equipped with Digital Card Scan 71 having the ability to scan a user's identification card and transmit the individual's name to LCD 61 of FIG. 5.

Figure 6B:
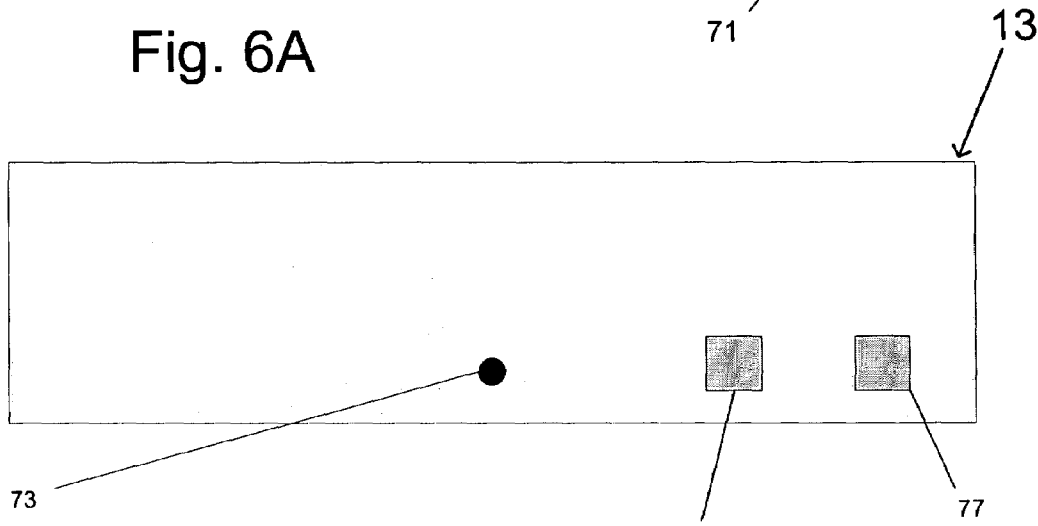
FIG. 6B depicts a rear view of the interface shown in FIG. 6A, showing electrical connection and outgoing data flow means for transferring collected information to the system.

Referring next to FIG. 6B, a rear view of EIS Machine 13 is depicted, including electrical plug 73 for supplying power to EIS Machine 13. In addition, it is preferable to have communication lines connected from EIS Machine 13 to outgoing server port 75 (e.g., communication line 15 of FIG. 1) and to an IAD access port 77 (e.g., communication line 17 of FIG. 1). In the preferred embodiment, outgoing server port only handles outgoing data and the electrical plug is fixed in position. Alternate embodiments of the invention include portable EIS Machines powered by batteries, fuel cells or other available power source.

Figure 6C:
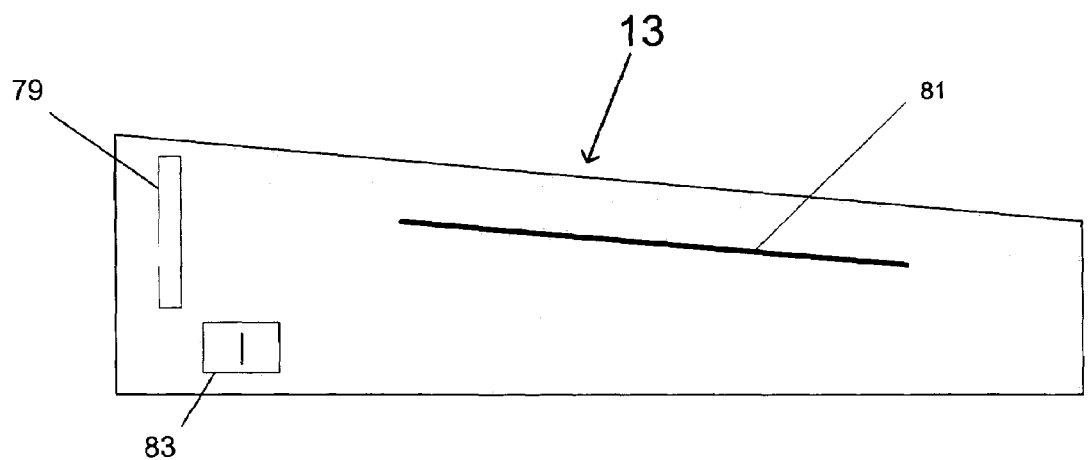
FIG. 6C depicts a side view of the interface shown in FIG. 6A, showing a locator device and a writing utensil for use in signature confirmation.

Referring next to FIG. 6C, shown is a side view of EIS Machine 13, including GPS Antenna 79 for transmitting the location of EIS Machine 13 to EISCAP 3 during the authentication process. EIS Machine 13 also comprises EIS Pick 81, a utensil to allow a user to sign his or her signature on EIS Rink 69. In addition, the preferred embodiment of EIS Machine 13 contains On/Off Switch 83 to control whether the machine is accessible at any given time.

Referring next to FIG. 7, a cross section of the internal hardware of the preferred embodiment of EIS Machine 13 is depicted.

Specifically, as shown in FIG. 7, hardware for LCD 61, EIS Keys 63 digital camera 65, EIS Crystal 67 and EIS Rink 69 (e.g., signature pad). In addition, hardware for digital card scan 71 is present within EIS Machine 13. Memory 85 is located within EIS Machine 13 to store the information entered by the user. In the preferred embodiment of the present invention, memory 85 is flash memory and is erased entirely following each transaction. In this manner, no information is locally stored in EIS Machine 13 for any extended period of time, thereby eliminating any risk of user confidential information being stolen from EIS Machine 13.

Referring next to FIG. 8, shown is the hardware configuration of the preferred embodiment of EIS Machine 13 of the present invention. As depicted in FIGS. 5 and 7, FIG. 8 shows LCD 61, Camera 65 and Card Reader 71. The preferred embodiment of EIS Machine 13 of the present invention further comprises circuit board 91 for connecting to the power source and the cover/screw entrance security system. Network Adapter 93 can comprise any standard network adapter for use with any high-speed data transfer connection, including wireless communication. Network adapter 93 is optimally configured to include encryption such that data is always forwarded across the network in a secure manner. GPS transmission device 95 can be activated for every data transmission to retrieve information to be sent to EISCAP 3. GPS transmission device 95 can also be activated by EISCAP 3 in order to implement routine security checks.

Figure 9A:
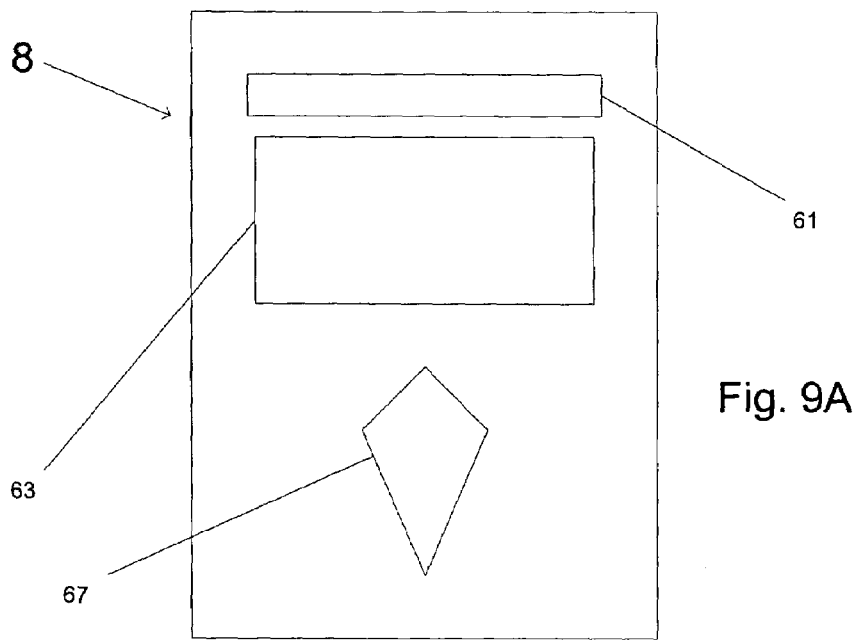
FIG. 9A depicts a front view of the EIS Maker of the present invention, which is an alternative embodiment to the EIS Machine shown in FIG. 5, without a digital camera, EIS Rink, or EIS Tray.
Figure 9B:
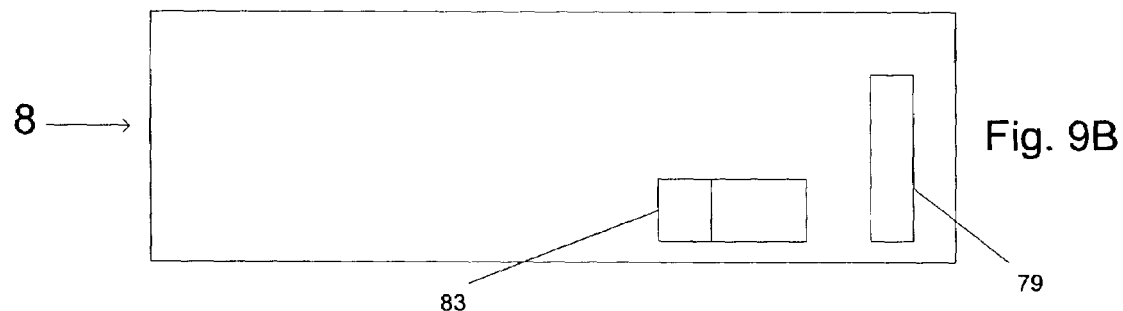
FIG. 9B depicts a side view of the EIS Maker shown in FIG. 9A, showing a locator device and a power switch.
Figure 9C:
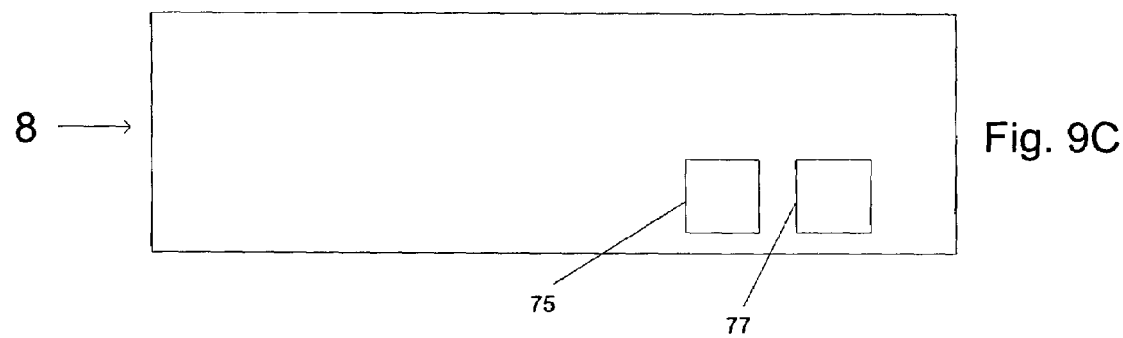
FIG. 9C depicts a rear view of the EIS Maker shown in FIG. 9A, showing electrical connection and outgoing data flow means for transferring collected information to the system.

FIGS. 9A-9C demonstrate a configuration of EIS Maker 8 which may in its present form accomplish similar tasks of EIS Machine 13 as in FIG. 1. For identification purposes it only contains the biometric device (e.g., EIS Crystal 67 in this representation) and EIS Keys 63 for identification number. It would be used when more complete forms of identification are not required such as with a repeat user.

While the above description describes the preferred embodiment as it relates to obtaining authenticated consent forms, other embodiments of the present invention exist as well. FIGS. 10-16 generally depict several alternate embodiments of the present invention.

Figure 10:
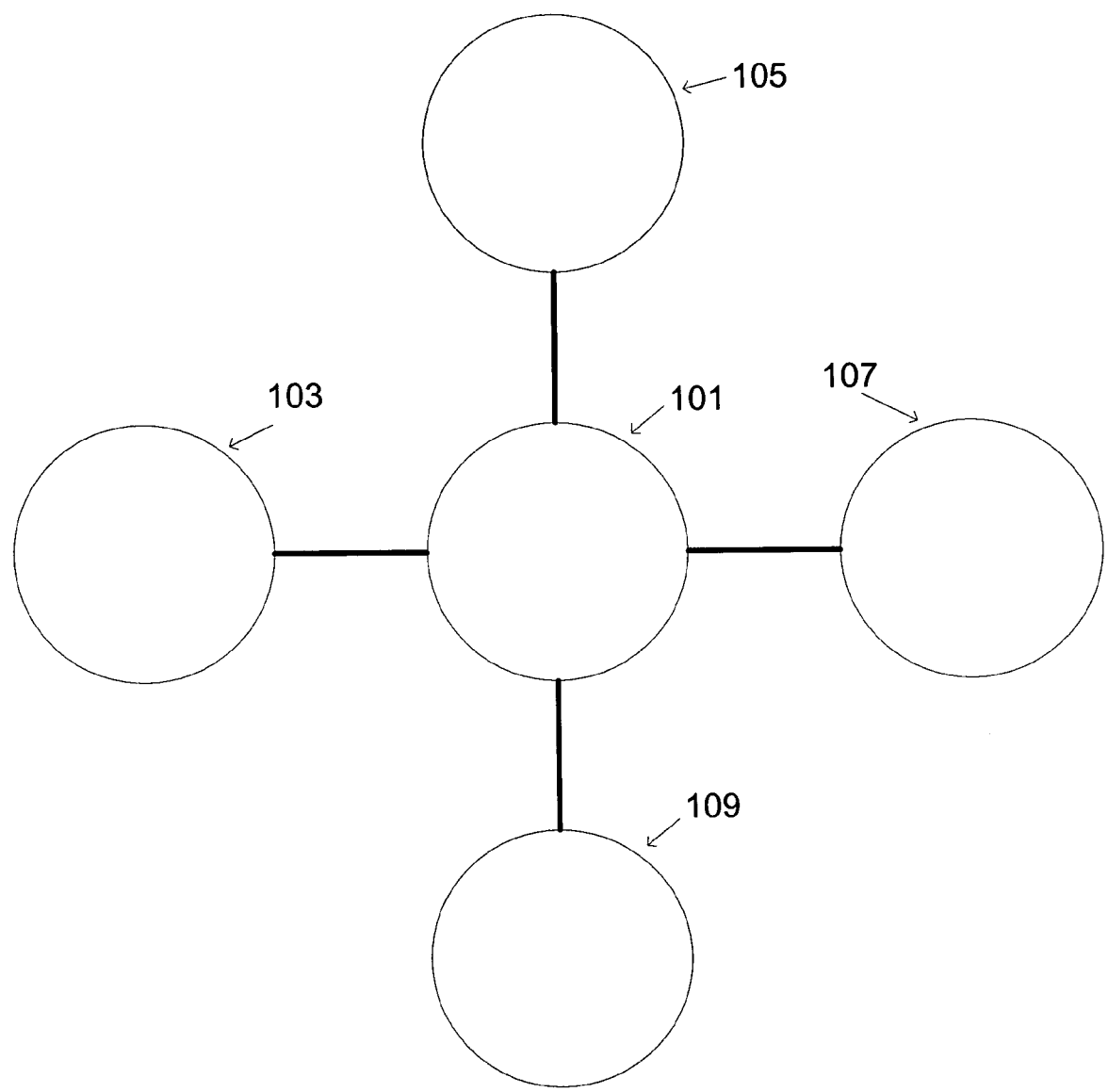
FIG. 10 depicts the ANI Network, which will exist for every individual that comes into the EISFLOE, shown in FIG. 1, comprising four complexes: Dianoian, Levavian, Nepheshian, and Meodian.

FIG. 10 represents an ANI Network (Automated Numerical Identifier Network) and a conceivable connection of EISBERGs. An ANI Network may be unique to every individual and is composed of multiple EISBERGs. In the preferred embodiment, an ANI Network is composed of EISBERGs that are structured to form groups, which are then structured to form systems. Systems are structured to form complexes, which ultimately form an ANI Network. Each individual's ANI Network 101 may contain multiple complexes. FIG. 10 depicts a preferred embodiment of a structure of complexes, namely the Dianoian Complex 103, Levavian Complex 105, Nepheshian Complex 107 and Meodian Complex 109. A complex may be broken down into systems of EISBERGS, as clarified below with respect to FIGS. 11-14. In the preferred embodiment, the Dianoian Complex 103 refers to the complex of EISBERGs in the ANI Network that are contained in the individuals' educational system, intellectual system, and personality system. It is intended to cover all aspects of activities, business, and transactions primarily related to the individuals' "mind" and its development. The Levavian Complex 105 refers to the complex of EISBERGs in the ANI Network that are contained in the individuals' habitual system, charitable system, and preferential system. It is intended to cover all aspects of activities, business, and transactions primarily related to the individual's "emotion" and its development. The Nepheshian Complex 107 refers to the complex of EISBERGs in the ANI Network that are contained in the individuals' political system, philosophical system, and religious system. It is intended to cover all aspects of activities, business, and transactions primarily related to the individuals' "soul" and its development. The Meodian Complex 109 refers to the complex of EISBERGs in the ANI Network that are contained in the individuals' medical system, legal system, vocational system, financial system, and relational system. It is intended to cover all aspects of activities, business, and transactions primarily related to the individuals' "strength" and its development.

Figure 11:
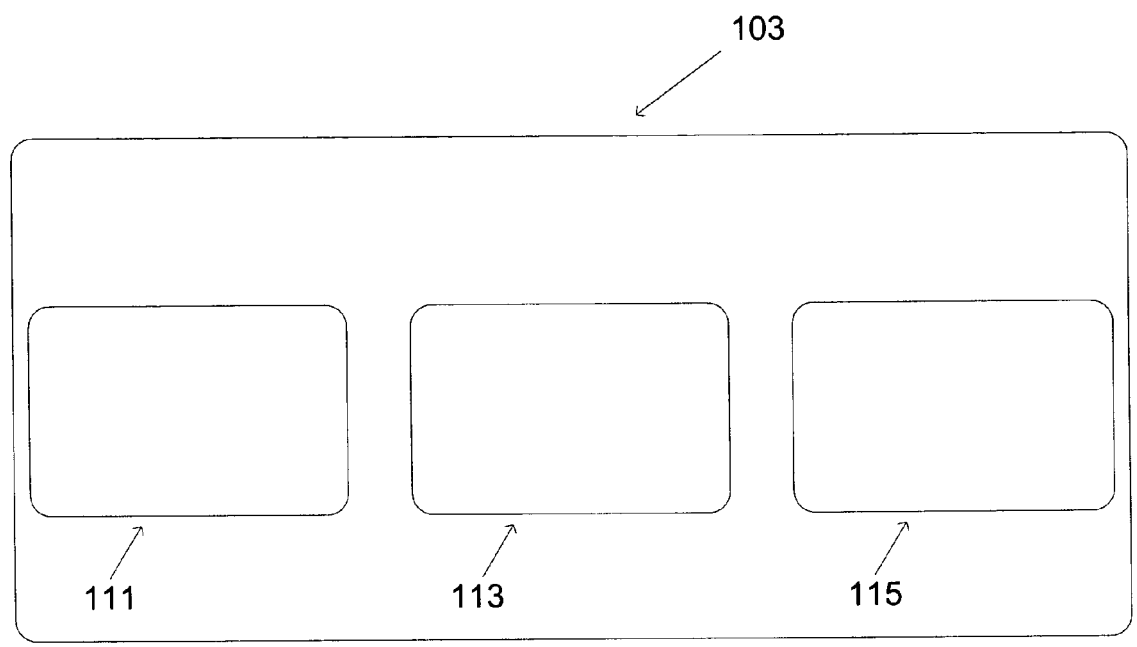
FIG. 11 depicts the Dianoian Complex shown in FIG. 10, comprising three Systems: Educational, Intellectual, and Personality.

FIG. 11 depicts the structure of three systems of EISBERGs that comprise the Dianoian Complex 103. The Educational System ("Minerva") 111, Intellectual System ("Athena") 113 and Personality System ("Galen") 115 are each composed of groups of EISBERGs. Together, the three systems form the Dianoian Complex 103.

Figure 12:
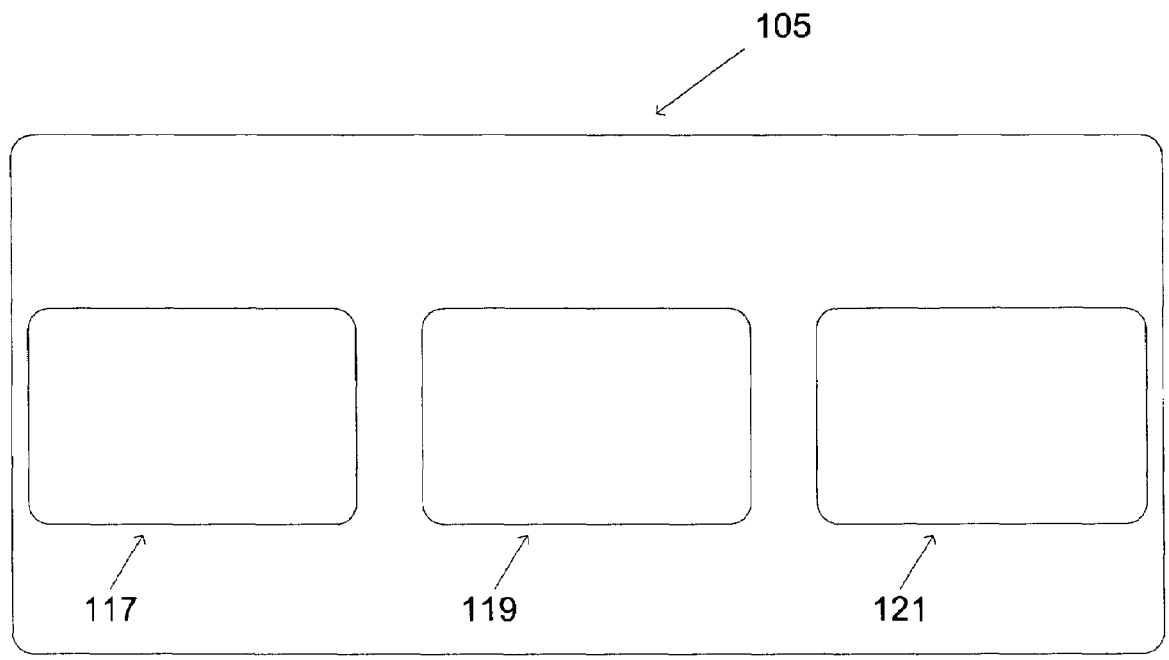
FIG. 12 depicts the Levavian Complex shown in FIG. 10, comprising three Systems: Habitual, Charitable, and Preferential.

FIG. 12 depicts the structure of three systems of EISBERGs that comprise the Levavian Complex 105. The Habitual System ("Artemis") 117, Charitable System ("Hestia") 119 and Preferential System ("Apollo") 121 are each composed of groups of EISBERGs. Together, the three systems form the Levavian Complex 105.

Figure 13:
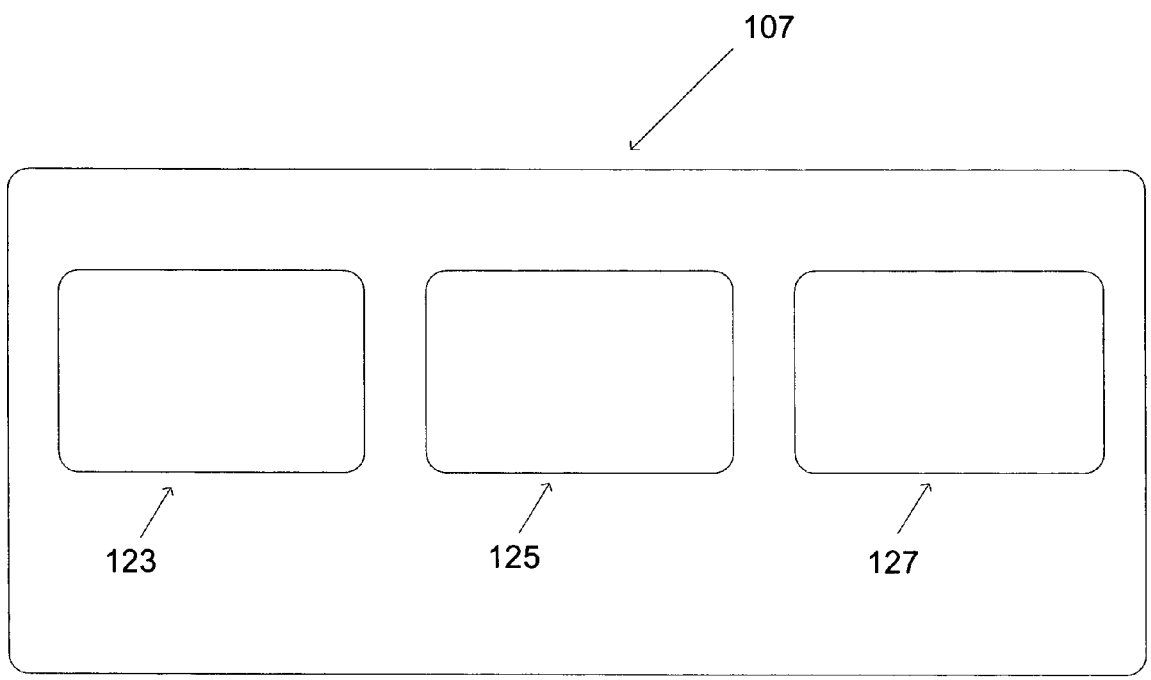
FIG. 13 depicts the Nepheshian Complex shown in FIG. 10, comprising three Systems: Political, Philosophical, and Religious.

FIG. 13 depicts the structure of three systems of EISBERGs that comprise the Nepheshian Complex 107. The Political System ("Zeus") 123, Philosophical System ("Thales") 125 and Religious System ("Enlil") 127 are each composed of groups of EISBERGs. Together, the three systems form the Nepheshian Complex 107.

Figure 14:
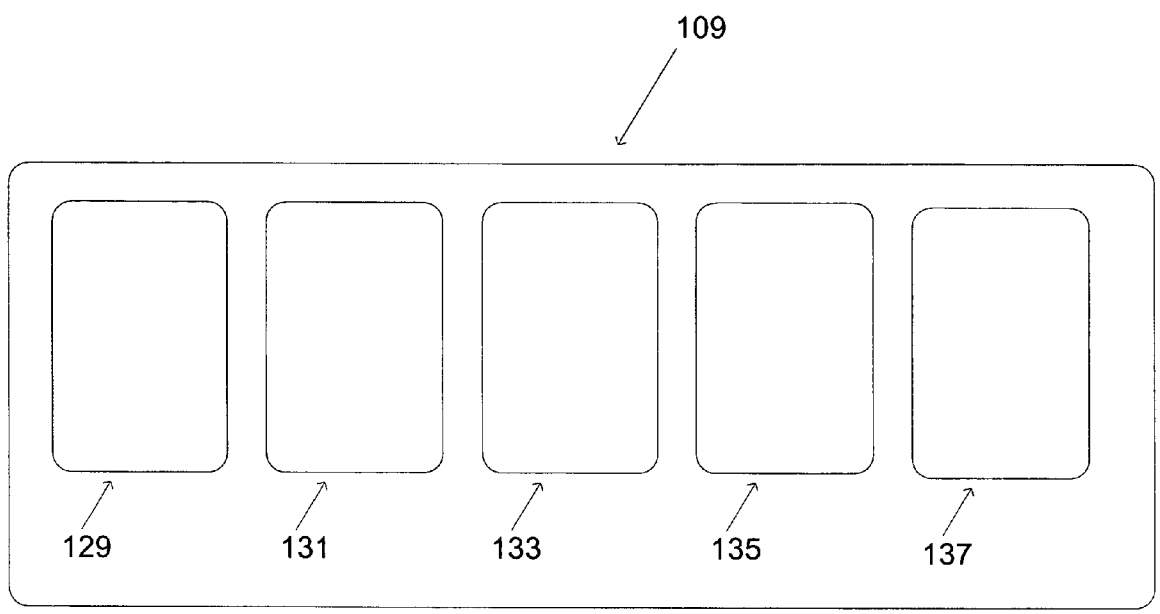
FIG. 14 depicts the Meodian Complex shown in FIG. 10, comprising five Systems: Medical, Legal, Vocational, Financial, and Relational.

FIG. 14 depicts the structure of three systems of EISBERGs that comprise the Meodian Complex 109. The Medical System ("Asklepios") 129, Legal System ("Hammurabi") 131, Vocational System ("Demeter") 133, Financial System ("Plutus") 135 and Relational System ("Hera") 137 are each composed of groups of EISBERGs. Together, the five systems form the Meodian Complex 109.

Figure 15:
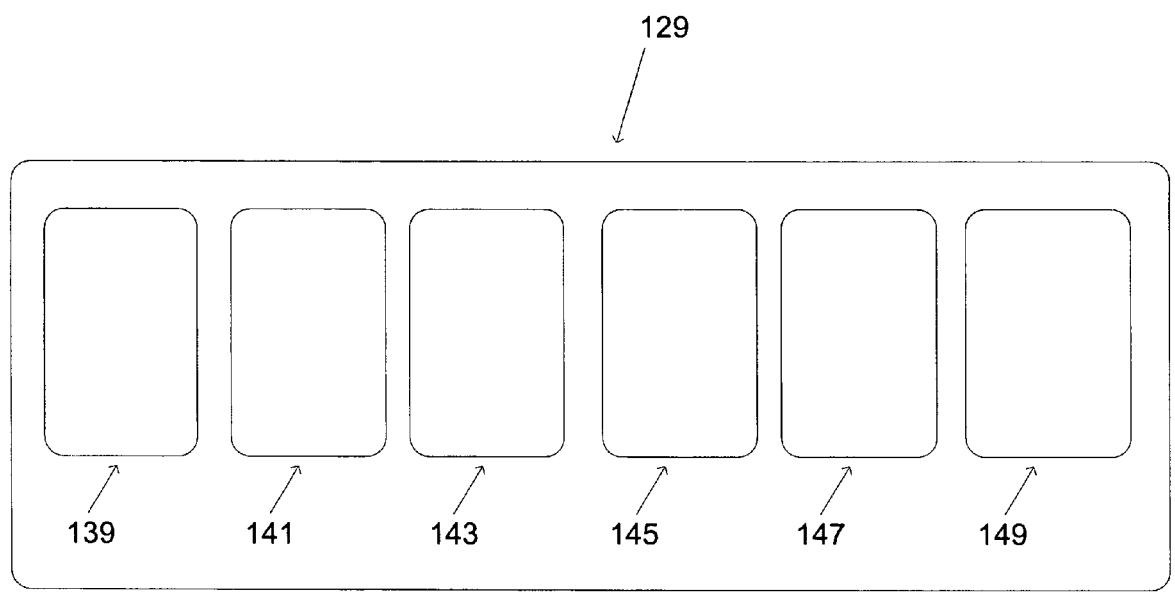
FIG. 15 depicts the Medical System ("Asklepios") shown in FIG. 10, comprising six Groups: Epione, Hygeia, Algla, Iasis, Akesis, and Panacea.

FIG. 15 represents the structure of Medical System 129, a component of the Meodian Complex 109 as depicted in FIG. 14. Medical System 129 is comprised of Soothing Arts and Sciences Group ("Epione") 139, Health Maintenance Group ("Hygeia") 141, Physical Beauty Arts and Science Group ("Aigla") 143, Healing Treatment Centers Group ("Iasis") 145, Convalescence Arts and Sciences Group ("Akesis") 147 and Pharmaceutical, Biotechnology, and Medical Equipment Group ("Panacea") 149. Each group is comprised of EISBERGs which represent the smallest entity that may store information. Each EISBERG is an independent unit capable of releasing information about an individual. Each individual may elect preferences as to how each EISBERG will release the individual's information. A plexus refers to the communication of various EISBERGs that an individual has linked together between and/or within groups, systems, or complexes that have been given authority by the individual to communicate information within the individual's ANI Network.

Figure 16:
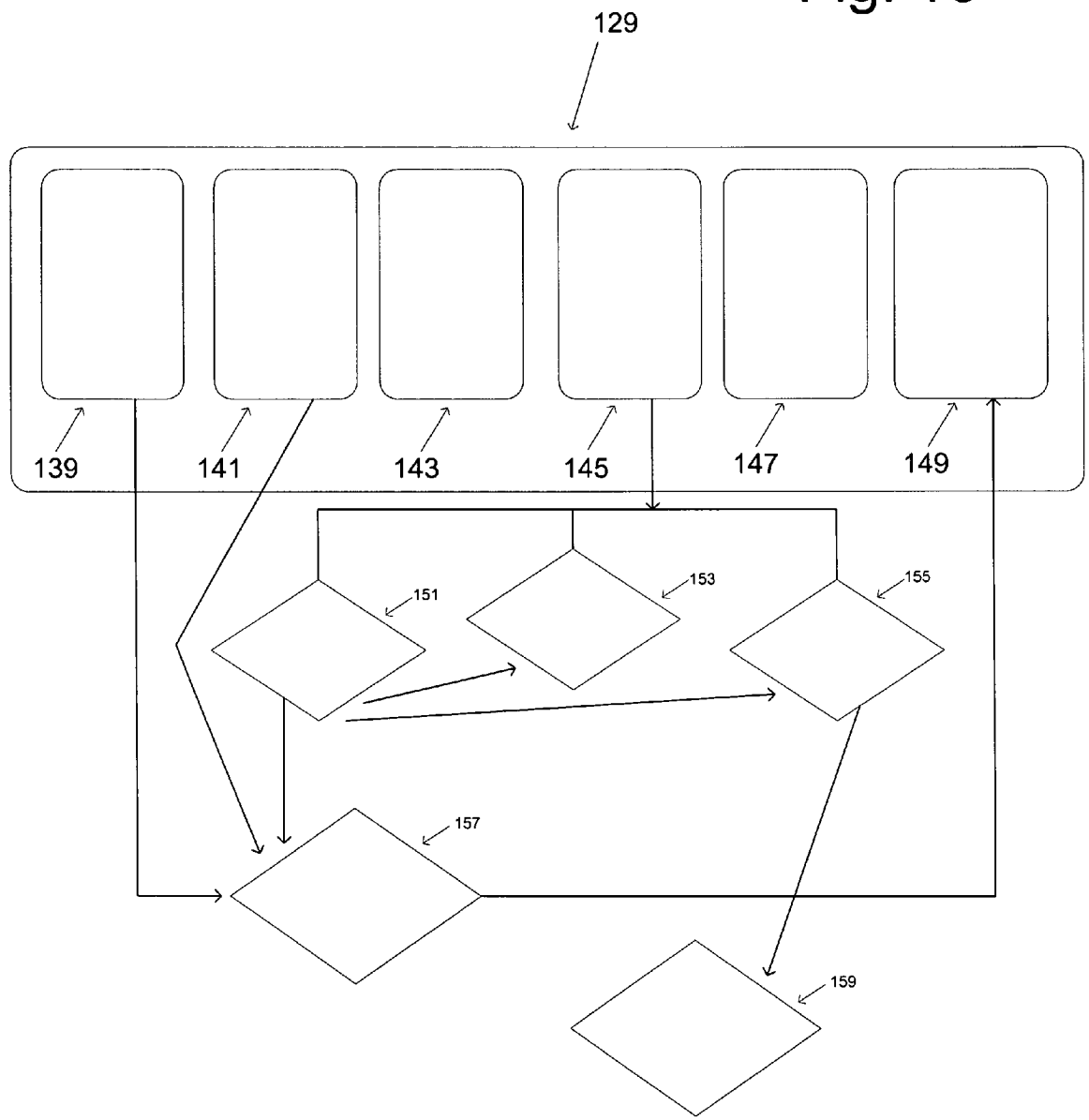
FIG. 16 depicts an example of a plexus of interaction between EISBERGs if an individual so authorizes. A Mede-Plexus of ACB EISBERG in Asklepios is denoted. Arrows represent authorization points before personal data is transmitted.

FIG. 16 represents a plexus formed in the Medical System 129 by the interaction of four groups of EISBERGs with independent organizations. Arrows represent authorization points before data is transmitted. Epione 138 and Hygeia 141 transmit information to Medical Research Organization 157. Iasis 145 transmits information to Physician Clinics 151, Hospital Companies 153 and American Cancer Biorepository Organization 155. Physician Clinics 151 transmits information to Medical Research Organization 157, Hospital Companies 153 and American Cancer Biorepository Organization 155. State Cancer Registry Agency 159 receives information from American Cancer Biorepository Organization 155, while Panacea 149 receives information from American Cancer Biorepository Organization 155 and Medical Research Organization 157.

While the present invention has been described with reference to one or more preferred embodiments, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. An apparatus for providing an individual's authorized consent forms comprising:
    (a) a computer system comprising:
    first input means for receiving said individual's identification information; and
    second input means for receiving said individual's biometric information;
    (b) a database connection system comprising: a database comprising an individual's identification information and an individual's biometric information; at least one recording means for recording additional identification data indicating the time and/or location of receipt of the individual's identification information and biometric information; a database comprising the additional identification data; and verification means for authenticating the identity of said individual by verifying said individual's identification information and said individual's biometric information;
    (c) authorization means for recording said individual's consent on a consent form, wherein the authorization means is located remotely from the systems defined by (a) and (b) which are located remotely from each other; and
    (d) at least five communication lines: a first communication line for transmitting information from (a) to (b); a second communication line for transmitting information from (a) to (c); a third communication line for transmitting information from (c) to (a); a fourth communication line for transmitting information from (b) to (c); and a fifth communication line for transmitting information from (c) to (b).

2. An apparatus according to claim 1, wherein said identification information is a unique number.

3. An apparatus according to claim 1, wherein said second input means is a fingerprint scanner.

4. An apparatus according to claim 1, further comprising at least one storage means for storing said authorized consent forms.

5. An apparatus according to claim 1, wherein location of receipt of the individual's identification information is determined by a global positioning system in communication with the database integration system.

6. An apparatus according to claim 1, wherein the database integration system further comprises a security apparatus to prevent fraudulent use of said apparatus.

7. An apparatus according to claim 1, wherein said first input means and said second input means are located remotely from said verification means and said authorization means.

8. An apparatus according to claim 1, wherein the computer system defined by (a) further comprises an internet access device (IAD) such that the first communication line transmits information from the IAD to (b), and the second communication line transmits information from (b) to the IAD.

9. An apparatus for providing authorized consent forms comprising:
    a first computer device for receiving an individual's identification information;

a second computer device for authenticating the identity of said individual; and a third computer device for recording authorized consent forms, wherein information flow between the first and second computer devices is unidirectional while information flow between the first and third computer devices and the second and third computer devices is bi-directional.

10. An apparatus according to claim 9, wherein said first computer device receives said individual's biometric information.

11. An apparatus according to claim 10, wherein said first computer device comprises a fingerprint scanner.

12. An apparatus according to claim 9 wherein said identification information is a unique number.

13. An apparatus according to claim 9, wherein said third computer device comprises a database for storing consent forms.

14. An apparatus according to claim 9 wherein any of said first computer device, said second computer device, said third computer device are located in a composite unit.

15. An apparatus according to claim 9, wherein said first computer device comprises an electronic identification system (EIS) machine and an internet access device (IAD), wherein the individual's identification information is transmitted from the EIS machine to the IAD and a consent form is requested at the IAD.

16. An apparatus according to claim 15 wherein the EIS machine is incapable of receiving any electronically transmitted information.

* * * * *

UNITED STATES PATENT AND TRADEMARK OFFICE
CERTIFICATE OF CORRECTION

PATENT NO. : 7,298,872 B2 Page 1 of 1
APPLICATION NO. : 10/920078
DATED : November 20, 2007
INVENTOR(S) : Shawn Glisson It is certified that error appears in the above-identified patent and that said Letters Patent is hereby corrected as shown below:

On the Title Page, Item (54)
Change "ENDORSMENT" to -- ENDORSEMENT --.

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO.        : 7,298,872 B2
APPLICATION NO.   : 10/920078
DATED             : November 20, 2007
INVENTOR(S)       : Shawn Glisson Page 1 of 1

It is certified that error appears in the above-identified patent and that said Letters Patent is hereby corrected as shown below:

On the Title Page, Item (54) and Column 1, line 3,
Change "ENDORSMENT" to -- ENDORSEMENT --.

This certificate supersedes the Certificate of Correction issued November 18, 2008.

Signed and Sealed this

Ninth Day of December, 2008

JON W. DUDAS
*Director of the United States Patent and Trademark Office*